US007121111B2

(12) United States Patent
Wilson et al.

(10) Patent No.: US 7,121,111 B2
(45) Date of Patent: Oct. 17, 2006

(54) APPARATUS AND METHOD FOR CHILLING BEVERAGES IN CONTAINERS

(75) Inventors: Jeffrey A. Wilson, Cleveland Heights, OH (US); Jonathan W. Flick, Mentor, OH (US)

(73) Assignee: Wendell-Alan Ltd., Cleveland, OH (US)

(*) Notice: Subject to any disclaimer, the term of this patent is extended or adjusted under 35 U.S.C. 154(b) by 0 days.

(21) Appl. No.: 11/161,484

(22) Filed: Aug. 4, 2005

(65) Prior Publication Data

US 2005/0257562 A1 Nov. 24, 2005

Related U.S. Application Data

(63) Continuation-in-part of application No. 10/298,453, filed on Nov. 18, 2002, now Pat. No. 7,060,086.

(51) Int. Cl.
*F25D 3/08* (2006.01)

(52) U.S. Cl. ........................................ 62/457.4; 62/371

(58) Field of Classification Search ............... 62/457.4, 62/457.2, 371, 530

See application file for complete search history.

(56) References Cited

U.S. PATENT DOCUMENTS

| | | | | |
|---|---|---|---|---|
| 3,302,428 | A * | 2/1967 | Paquin et al. | 62/457.4 |
| 4,468,933 | A * | 9/1984 | Christopher | 62/457.1 |
| 4,882,914 | A * | 11/1989 | Haines-Keeley et al. | 62/457.4 |
| 5,974,824 | A * | 11/1999 | Galockin et al. | 62/394 |
| 6,581,401 | B1 * | 6/2003 | Anthony | 62/293 |

* cited by examiner

*Primary Examiner*—Melvin Jones
(74) *Attorney, Agent, or Firm*—Rankin, Hill, Porter & Clark LLP

(57) ABSTRACT

The present invention provides an apparatus and method for chilling beverages in containers. The apparatus includes a tubular body having a first opening, a second opening, an inner surface and an outer surface. The first opening, the inner surface and the second opening cooperate to define a passage through the tubular body for receiving a beverage container. The inner surface and outer surface of the tubular body are formed of and defined by a continuous film of flexible material. A non-gaseous temperature-retaining fluid is received between the inner surface and the outer surface of the tubular body. The apparatus is pre-chilled prior to use, and then is rolled onto the beverage container such that the beverage container is received within the passage through the tubular body to rapidly chill the beverage to a desired serving temperature.

15 Claims, 5 Drawing Sheets

100
105
109
104
104
105
107

APPARATUS AND METHOD FOR CHILLING BEVERAGES IN CONTAINERS

CROSS-REFERENCE TO RELATED APPLICATION

This application is a continuation-in-part of application Ser. No. 10/298,453, filed Nov. 18, 2002, now U.S. Pat. No. 7,060,086.

BACKGROUND OF THE INVENTION

1. Field of Invention

The present invention relates to an apparatus and method for chilling beverages in containers.

2. Description of Related Art

Beverages are conveniently packaged in sealed containers such as aluminum cans, glass or plastic bottles, and paper cartons. Most beverage containers are shipped and stored at ambient temperature. Accordingly, the beverage containers must be placed into a refrigerated environment for a sufficient time to adequately chill the beverage to an appropriate serving temperature.

Chilling a beverage in a refrigerator can take several hours. The chilling process can be expedited by immersing the beverage container in an ice bath or by pouring the beverage from the container into a glass containing ice. But ice is not always available and some beverages such as wine, for example, are not ordinarily served over ice. An apparatus and method for rapidly chilling beverages in containers is needed.

BRIEF SUMMARY OF THE INVENTION

The present invention provides an apparatus and method for chilling beverages in containers that overcomes the limitations and disadvantages of the prior art. An apparatus according to the invention comprises a tubular body having a first opening, a second opening, an inner surface and an outer surface. The first opening, the inner surface and the second opening cooperate to define a passage through the tubular body for receiving a beverage container. The inner surface and outer surface of the tubular body are defined by a continuous film of flexible material such as, for example, a copolymer of polyester and polyurethane. A non-gaseous temperature-retaining fluid that does not become a hard solid at 32° F. (e.g., a water-based gel) is received between the inner surface and the outer surface of the tubular body. The apparatus is pre-chilled prior to use, typically by storing the apparatus in a freezer compartment of a refrigerator appliance. At the time of use, the pre-chilled apparatus is rolled onto the beverage container such that the beverage container is received within the passage through the tubular body. The diameter of the passage through the apparatus is preferably slightly smaller than the diameter of beverage container. Thus, when the inner surface of the tubular body makes contact with the outer surface of the beverage container, the continuous film of flexible material everts about the tubular body allowing the apparatus to roll onto and circumferentially surround the beverage container. The continuous film of flexible material can be everted about the tubular body as many times or cycles as is needed to position the device on the beverage container. Because the tubular body is filled with a temperature retaining fluid such as a water-based gel and is formed of flexible material, the tubular body conforms to the contours of the beverage container and maintains intimate contact with a substantial portion of the outer circumferential surface of the beverage container. The pre-chilled apparatus absorbs heat from the beverage stored in the beverage container and rapidly chill the beverage to serving temperature.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

DETAILED DESCRIPTION OF THE INVENTION

Figure 1:
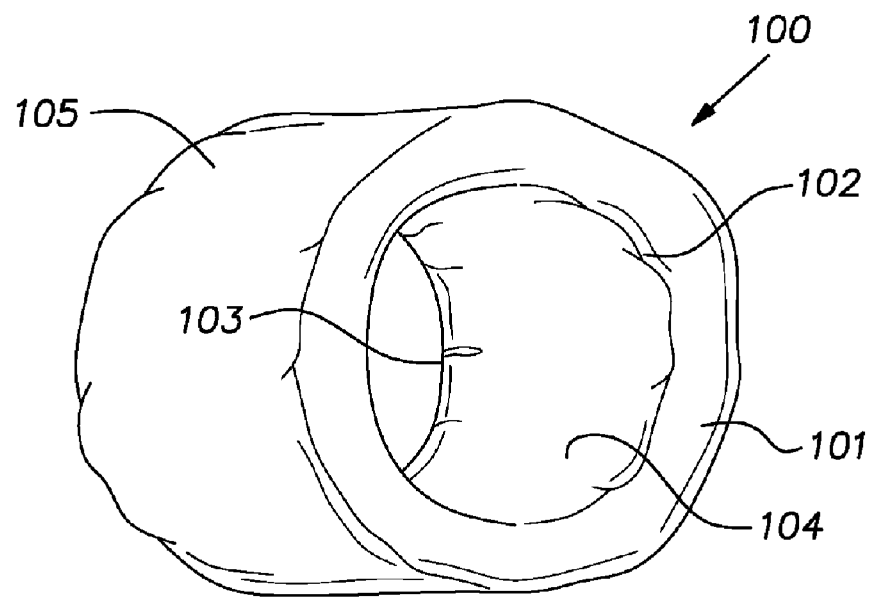
FIG. 1 is a perspective view of an exemplary embodiment of an apparatus according to the invention.
Figure 2:
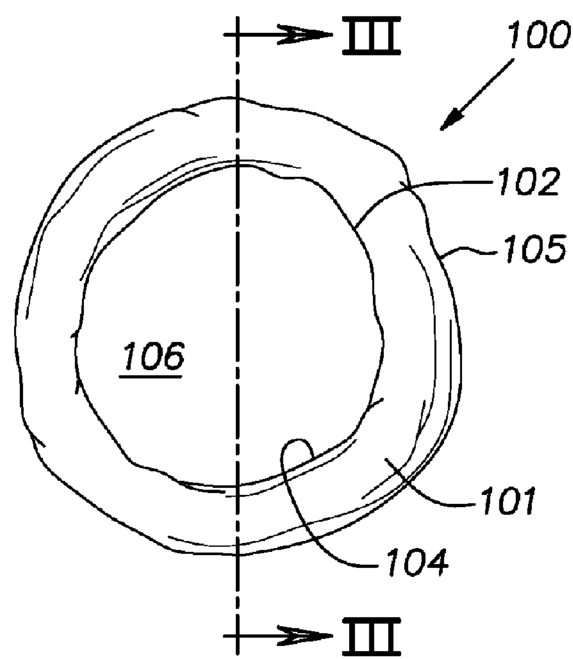
FIG. 2 is an end view of the apparatus shown in FIG. 1.
Figure 3:
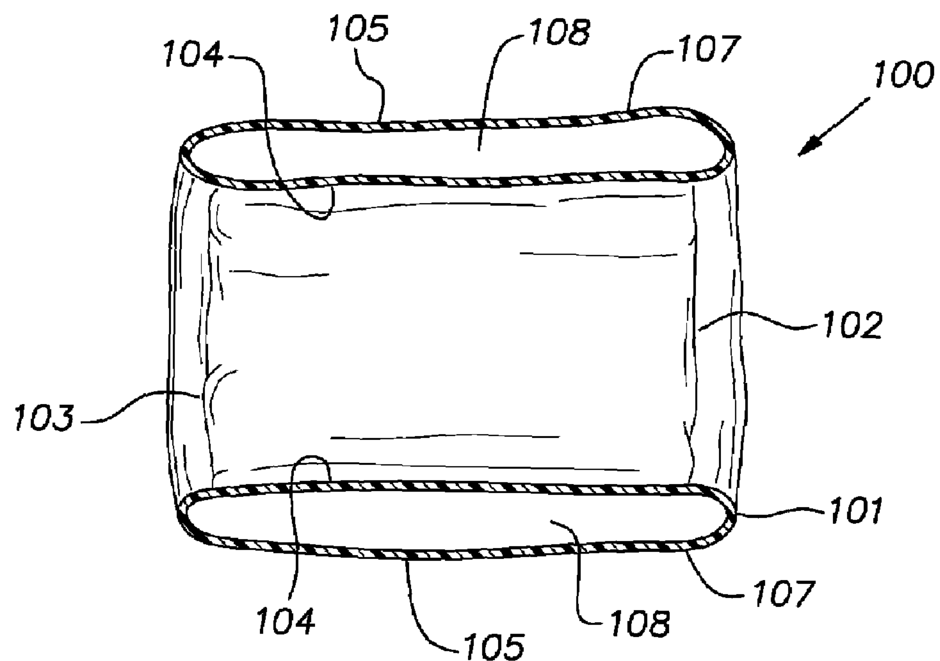
FIG. 3 is a cross-sectional view of the apparatus taken along the line III—III in FIG. 2.

With reference to the accompanying figures, and in particular FIGS. 1 and 2, an exemplary apparatus 100 according to the invention comprises a tubular body 101 having a first opening 102, a second opening 103, an inner surface 104 and an outer surface 105. The first opening 102, the inner surface 104 and the second opening 103 cooperate to define a passage 106 through the tubular body 101 for a beverage container. FIG. 3 is a view of the apparatus 100 as seen along the line 3—3 in FIG. 2. Thus, an apparatus 100 in accordance with the invention comprises a tubular body 101 having an elongated generally torus-like shape.

The tubular body 101 is formed of a continuous film of flexible material 107, which is preferably a polymeric film that remains flexible over a relatively broad temperature range of from about 0° F. to about 130° F. A large number of polymeric films that remain flexible over such a temperature range are known in the art. It will be appreciated that polymeric films used in the invention can be single layer films or multi-layer structures.

Preferably, the continuous film of flexible material exhibits a Shore A durometer hardness of greater than or equal to 85 as measured in accordance with the ASTM 2240.00 standard. More preferably, the continuous film of flexible material exhibits a Shore A durometer hardness of 93 ±5 as measured in accordance with the ASTM 2240.00 standard. Films possessing such properties are advantageously puncture resistant yet remain flexible.

The continuous film of flexible material preferably has a thickness of from about 3 to about 15 mils. More preferably, the continuous film of flexible material has a thickness of 5±2 mils. It will be appreciated that film thickness is not per se critical, and that a variety of film thicknesses can be used to fabricate an apparatus in accordance with the invention.

In the presently most preferred embodiment of the invention, the continuous film of flexible material comprises a 5 mil thick copolymer of polyester and polyurethane having a Shore A durometer hardness of about 95 as measured in accordance with the ASTM 2240.00 standard. This film provides several advantages. It can be heat-sealed to itself, which facilitates fabrication of the apparatus. And, it remains smooth and flexible over the temperature range of from about 0° F. to about 130° F.

A temperature-retaining fluid 108 is received into the space between the inner surface 104 and the outer surface 105. Throughout the instant specification and in the appended claims, the term "temperature-retaining fluid" means any non-gaseous material that changes shape or direction uniformly in response to an external force imposed upon it and that has the capacity to retain heat or cold for chilling a beverage. The term applies not only to liquids, but also to finely divided solids, gels and combinations of liquids and solid particles having such properties. Preferably, the temperature-retaining fluid is a gel, and more preferably a water-based gel.

Water-based gels can be formulated so as to provide a temperature-retaining fluid that is more viscous than water and does not become a hard solid within the temperature range of from 0° F. and 32° F. Such gels can easily conform to the outer circumferential contours of beverage containers. In addition, such gels tend to retain their desired thermal properties for a longer period of time than water. The composition of the gel is not per se critical, but preferably a non-toxic formulation is used to minimize potential injury in the event of unintended exposure.

In another embodiment of the invention, water-filled capsules are dispersed in the temperature-retaining fluid. When the apparatus is pre-chilled (e.g., by storing in a freezer compartment of a refrigerator appliance), the water in the water-filled capsules freezes and becomes solid ice, although the gel remains a viscous fluid. The frozen water-filled capsules extend the period of time during which the apparatus remains cold. The water-filled capsules are preferably small, such as the size of peas, and substantially spherical, which allows the apparatus to intimately contact the outer circumferential surface of beverage containers.

Other free-flowing solid structures can be dispersed in the temperature-retaining fluid. Examples include inorganic particulates (e.g., sand and/or ceramic particles), spherical structures (e.g., glass and/or metal spheres), magnets and combinations thereof. It will be appreciated that virtually any relatively small substantially free-flowing solid structure can be dispersed in the temperature-retaining fluid, but water-filled capsules are preferably most preferred in view of cost, safety, and effectiveness.

Figure 4:
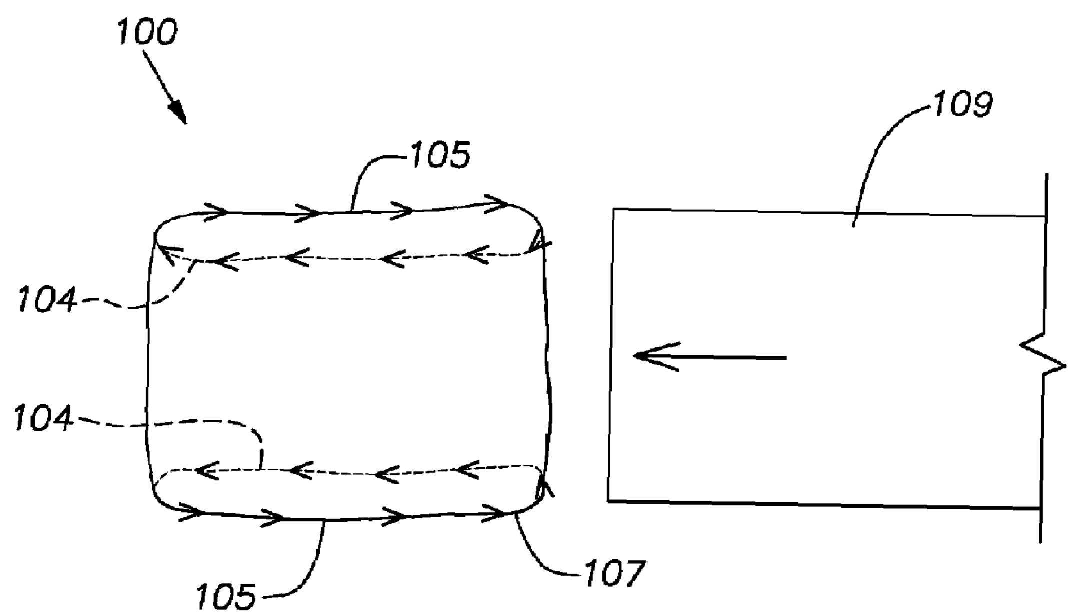
FIG. 4 is a schematic view of an exemplary apparatus according to the invention about to be rolled onto a beverage container.

FIG. 4 is a schematic view showing an apparatus 100 according to the invention as it is about to be placed onto a beverage container 109. The large arrow shown on the beverage container 109 shows the direction the beverage container moves relative to the apparatus 100. The series of small arrows shown on the inner surface 104 and the outer surface 105 of the apparatus 100 in FIG. 4 show the movement of the continuous film of flexible material 107 as the apparatus 100 rolls onto the beverage container 109. The diameter of the passage 106 through the tubular body 101 is preferably slightly smaller than the largest diameter of the beverage container 109. Thus, the continuous film of flexible material 107 frictionally engages the outer circumferential surface of the beverage container 109. The continuous film of flexible material 107 does not substantially slide relative to the circumferential surface of the beverage container 109, but tubular body defined by the continuous film of flexible material 107 everts as the apparatus 100 rolls onto the beverage container 109 in the direction opposite the large arrow, retaining its general torus-like shape as it conforms to the contours of the beverage container. As shown by the series of arrows in FIG. 4, the continuous film of flexible material 107 is eversion-limitless, meaning that the continuous film of flexible material 107 can be everted around the tubular body 101 from the inner surface 104 to the outer surface 105 and back an infinite number of cycles or revolutions in either direction.

It will be appreciated that the apparatus according to the invention can be formed in various sizes to accommodate beverage containers of various sizes. The longitudinal length of the tubular body 101 should be sufficient to allow the inner surface 104 of the tubular body to contact a substantial portion of the outer circumferential surface of the beverage container 109. The diameter of the passage through the tubular body 101 should be slightly smaller than the diameter of the beverage container 109 to facilitate contact between the inner surface 104 of the tubular body 101 and the outer circumferential surface of the beverage container 109. Larger apparatus can be used on wine bottles, 2-Liter plastic soda bottles and the like, whereas smaller apparatus can be used on 12-ounce aluminum cans and the like.

An apparatus comprising a tubular body 101 having a longitudinal length of about 4.0 to about 5.0 inches, and more preferably about 4.5 inches, and a passage with an inner diameter of about 2.0 to about 2.5 inches, or more preferably about 2.25 inches, is particularly suitable for use on a standard 12-ounce aluminum beverage can. Approximately 16 fluid ounces of gel material can be disposed into the space between the inner surface 104 and the outer surface 105 of the tubular body 101 of this size to provide a substantially uniform gel thickness of about 0.5 inches over a substantial portion of the outer surface of the aluminum beverage can when the apparatus 100 is disposed thereon. The longitudinal length and inner diameter of the passage through the tubular body 101 can be sized to accommodate beverage containers of virtually any size or shape.

Figure 5:
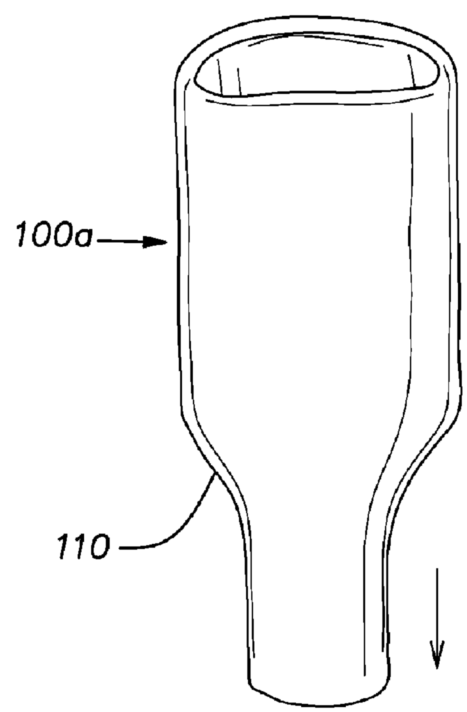
FIG. 5 is perspective view of another exemplary embodiment of an apparatus according to the invention as it is about to be rolled onto a wine bottle.
Figure 5:
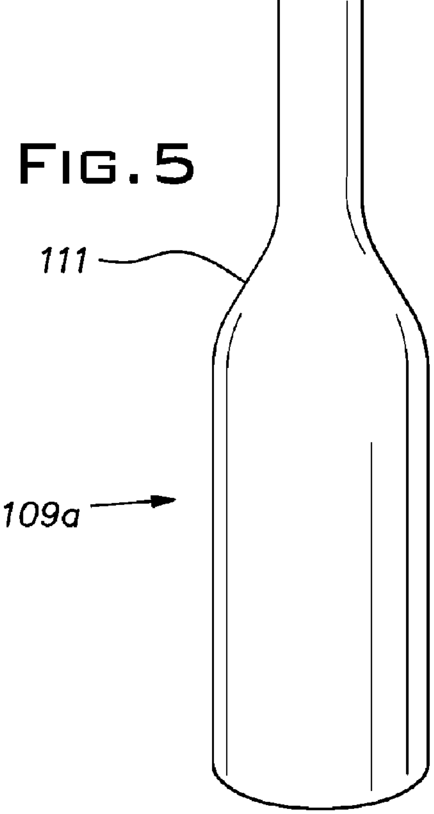
Figure 6:
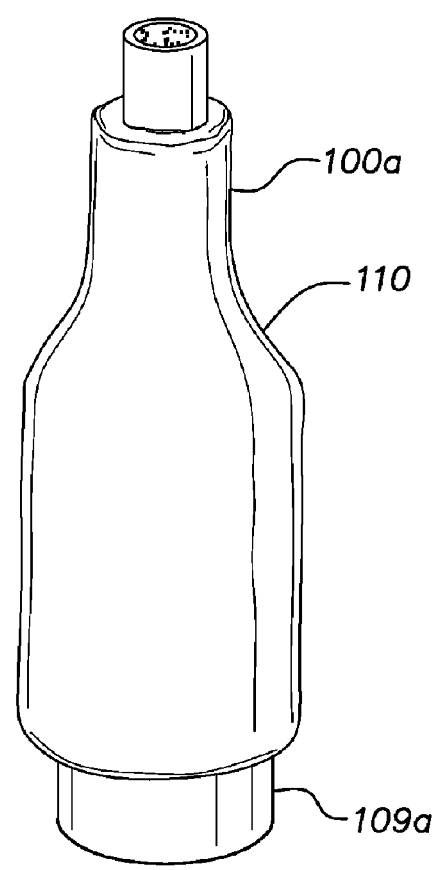
FIG. 6 is a perspective view of the apparatus shown in FIG. 5 disposed on the outer circumferential surface of the wine bottle.

FIG. 5 shows an alternative embodiment of an apparatus 100*a* according to the invention as it is about to be rolled onto a wine bottle 109*a*. The apparatus 100*a* includes a tapered section 110, which is configured to contact a shoulder portion 111 of the wine bottle 109*a* when the apparatus 100*a* is rolled onto the wine bottle 109*a*, such as shown in FIG. 6. The longitudinal length of the apparatus 100*a* is preferably from about 10.0 to about 13.0 inches. Methods of manufacturing apparatus according to the invention, including methods of manufacturing an apparatus including a tapered section, are described in application Ser. No. 10/298,453, filed Nov. 18, 2002, now U.S. Pat. No. ______, which is hereby incorporated by reference in its entirety.

Figure 7:
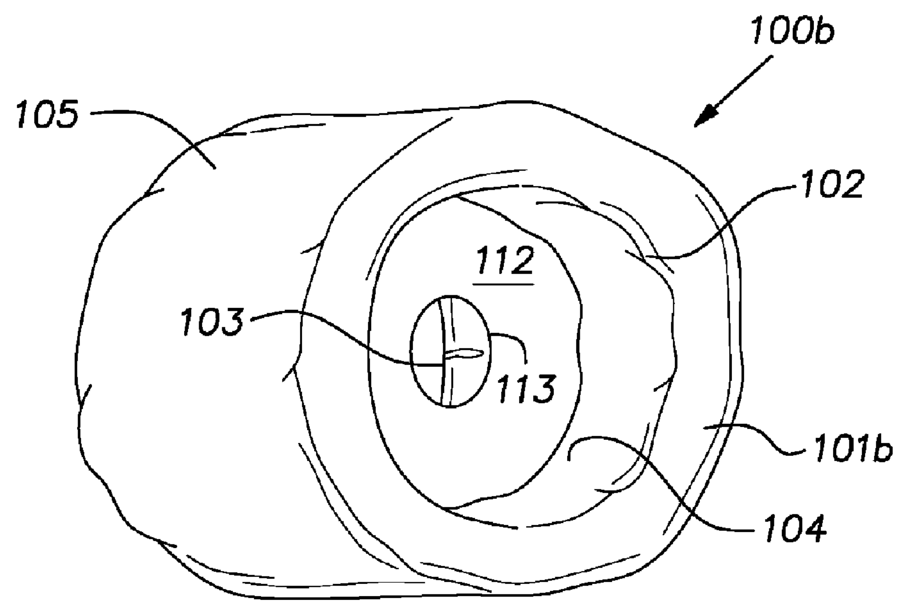
FIG. 7 is a perspective view of yet another exemplary embodiment of an apparatus according to the invention.

FIG. 7 shows yet another alternative embodiment of an apparatus 100*b* according to the invention. The apparatus 100*b* comprises a web portion 112 that spans the passage 106*b* through the tubular body 101*b*. The web portion 112 can, but need not necessarily, be provided with an opening 113 for receiving a portion of a beverage container, such as a neck portion of a glass or plastic bottle. The web portion 112 is preferably formed of the same flexible material as the tubular body 101*b*, and can thus be joined to the inner surface 104*b* of the tubular body 101*b* by heat sealing or other suitable means.

Figure 8:
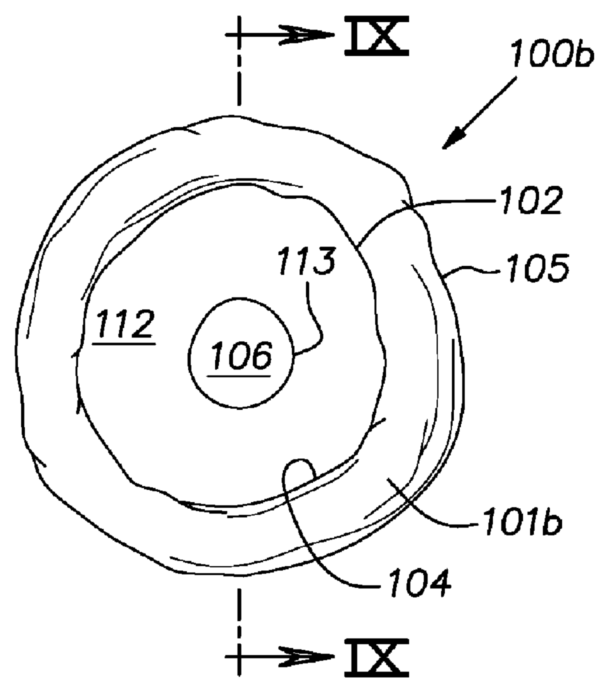
FIG. 8 is an end view of the apparatus shown in FIG. 7.
Figure 9:
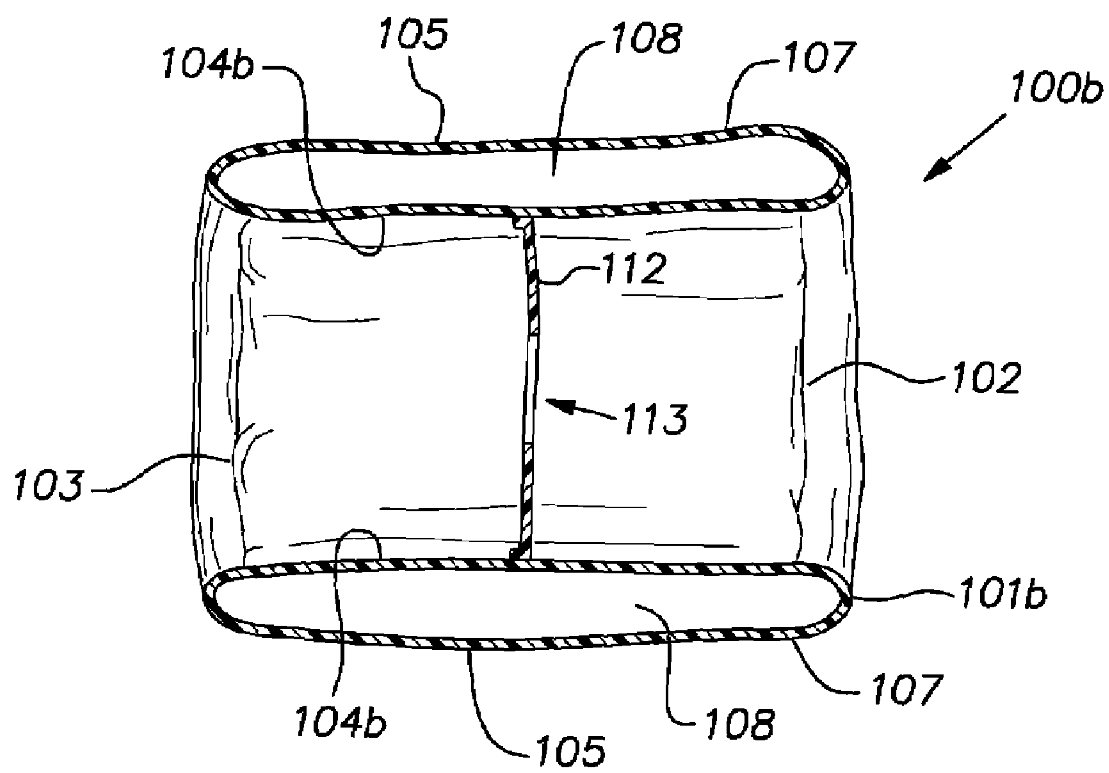
FIG. 9 is a cross-sectional view of the apparatus taken along the line IX—IX in FIG. 8.

FIG. 8 shows an end view of the apparatus 100*b* shown in FIG. 7. FIG. 9 shows a sectional view of the apparatus 100*b* shown in FIG. 8 taken along the line IX—IX. A beverage container such as an aluminum can or a glass or plastic bottle, is positioned such that one end is adjacent to (or is passed through the optional opening 113 in) the web portion of the apparatus 100*b*. The tubular body 101*b* of the pre-chilled apparatus 100*b* is then rolled onto the outer circumferential surface of the aluminum can or glass or plastic bottle to chill the beverage inside the container. The web portion 112 helps keep the apparatus 100*b* from slipping off the container during chilling, and when provided with an opening 113, allows a user to consume the beverage from the container while the apparatus 100*b* is positioned on the container.

As noted above, the apparatus according to the invention must be pre-chilled prior to use. Pre-chilling can be accomplished by storing the apparatus in a freezer or the freezer compartment of a refrigerator appliance. The temperature retaining fluid does not freeze and form a hard solid material at such temperatures, but remains pliable and can easily conform to the contours of the outer circumferential surface of a beverage container. The apparatus according to the invention can chill a 12-ounce beverage in an aluminum can that has been stored at room temperature (~70° F.) to a proper serving temperature (~34° F.) in less than about five minutes. Chilling is so rapid that ice crystals sometimes form in the beverage.

The apparatus according to the invention can also be used to heat beverages in containers. On particularly useful application is the heating of infant formula, previously expressed breast milk or other baby foods. In the past, infant formula and breast milk have been heated in baby bottles by immersing the bottles in heated water baths or by placing the bottles in specially configured electrically powered baby bottle heating devices. It would be desirable to heat baby bottles using a microwave oven, but due to the tendency of microwave ovens to heat fluid volumes unevenly, which can create localized "hot spots" that are not detectable upon removal of the bottle from the oven, such a practice is discouraged because it could lead to burning or scalding of infants. In addition, some containers, particularly metal containers, cannot be placed in microwave ovens.

In accordance with an alternative method of the invention, the apparatus is pre-heated using a microwave oven. The pre-heated apparatus is removed from the oven and rolled onto a beverage container in the same manner previously described. In this embodiment of the invention, the heated temperature retaining fluid transfers heat to the beverage stored within the container. Because the heat is transferred circumferentially to the bottle, localized heating is not a problem and precise temperature control can be obtained. The device can be rolled onto an opened food or beverage container to reheat the food or beverage therein.

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

What is claimed is:

1. A method of chilling a beverage in a container comprising: providing an apparatus comprising a tubular body having a first opening, a second opening, an inner surface and an outer surface, wherein the first opening, the inner surface and the second opening cooperate to define a passage through the tubular body, wherein the inner surface and the outer surface of the tubular body are defined by a continuous film of flexible material, wherein a non-gaseous temperature retaining fluid that does not become a hard solid at 32° F. is received between the inner surface and the outer surface of the tubular body; pre-chilling the apparatus to a temperature at or below a desired serving temperature of the beverage in the container; and disposing the inner surface of the pre-chilled apparatus such that it is in contact with an outer circumferential surface portion of the container for a period of time sufficient to chill the beverage to the desired serving temperature.

2. The method according to claim 1 wherein the container is an aluminum can, a plastic or glass bottle or a paper carton.

3. The method according to claim 1 wherein the container is a glass bottle and the beverage is wine.

4. The method according to claim 1 wherein the inner surface of the pre-chilled apparatus is disposed in contact with the outer circumferential surface portion of the container by inserting the container into the passage through the apparatus and rolling the apparatus onto the container such that the film of flexible material everts about the tubular body.

5. The method according to claim 1 wherein the non-gaseous temperature retaining fluid is a water-based gel.

6. The method according to claim 5 wherein free-flowing solid structures are dispersed in the gel.

7. The method according to claim 6 wherein the free-flowing solid structures are selected from the group consisting of water-filled capsules, inorganic particulates, glass spheres, metal spheres and combinations thereof.

8. The method according to claim 1 wherein the tubular body comprises a tapered section.

9. The method according to claim 1 wherein a web portion that spans the passage through the tubular body.

10. The method according to claim 9 wherein the web portion is provided with an opening for receiving a neck portion of a beverage container.

11. The method according to claim 1 wherein the continuous film of flexible material comprises a copolymer of polyester and polyurethane.

12. An apparatus for chilling a beverage in a container that has a body portion and a shoulder portion that is smaller in diameter than the body portion, the apparatus comprising a tubular body having a first opening, a second opening, an inner surface and an outer surface, wherein the first opening, the inner surface and the second opening cooperate to define a passage through the tubular body, wherein the inner surface and the outer surface of the tubular body are defined by a continuous film of flexible material that is evertible about the tubular body, wherein a non-gaseous temperature retaining fluid that does not become a hard solid at 32° F. is received between the inner surface and the outer surface of the tubular body, and wherein the tubular body includes a tapered section for contacting the shoulder portion of the container and a generally cylindrical portion for contacting the body portion of the container.

13. An apparatus for chilling a beverage in a container that has a body portion and a shoulder portion that is smaller in diameter than the body portion, the apparatus comprising a tubular body having a first opening, a second opening, an inner surface, an outer surface, and a web portion that spans the passage through the tubular body, wherein the first opening, the inner surface and the second opening cooperate to define a passage through the tubular body, wherein the inner surface and the outer surface of the tubular body are defined by a continuous film of flexible material, wherein a non-gaseous temperature retaining fluid that does not become a hard solid at 32° F. is received between the inner surface and the outer surface of the tubular body, and wherein the tubular body includes a tapered section for contacting the shoulder portion of the container and a generally cylindrical portion for contacting the body portion of the container.

14. The apparatus according to claim 13 wherein an opening is formed in the web portion for receiving a neck portion of the container.

15. A method of heating a food or a beverage in a container comprising: providing an apparatus comprising a tubular body having a first opening, a second opening, an inner surface and an outer surface, wherein the first opening, the inner surface and the second opening cooperate to define a passage through the tubular body, wherein the inner surface and the outer surface of the tubular body are defined by a continuous film of flexible material, wherein a non-gaseous temperature retaining fluid is received between the inner surface and the outer surface of the tubular body; pre-heating the apparatus using microwave radiation to a temperature at or above a desired serving temperature of the food or beverage in the container; and disposing the inner surface of the pre-heated apparatus such that it is in contact with an outer circumferential surface portion of the container for a period of time sufficient to heat the food or beverage to the desired serving temperature.

* * * * *